US012419665B2

(12) United States Patent
Lobo et al.

(10) Patent No.: US 12,419,665 B2
(45) Date of Patent: *Sep. 23, 2025

(54) SURGICAL ACCESS DEVICE WITH ROTATABLY ACTUATED FIXATION MECHANISM

(71) Applicant: Covidien LP, Mansfield, MA (US)

(72) Inventors: Astley C. Lobo, West Haven, CT (US); Oksana Buyda, East Haven, CT (US); Christopher A. Tokarz, Torrington, CT (US); Kevin Desjardin, Prospect, CT (US); Amanda M. Adinolfi, Wallingford, CT (US); Douglas M. Pattison, East Hartford, CT (US)

(73) Assignee: Covidien LP, Mansfield, MA (US)

( * ) Notice: Subject to any disclaimer, the term of this patent is extended or adjusted under 35 U.S.C. 154(b) by 153 days.

This patent is subject to a terminal disclaimer.

(21) Appl. No.: 18/206,793

(22) Filed: Jun. 7, 2023

(65) Prior Publication Data
US 2023/0310026 A1   Oct. 5, 2023

Related U.S. Application Data

(63) Continuation of application No. 16/784,662, filed on Feb. 7, 2020, now Pat. No. 11,672,563.

(51) Int. Cl.
A61B 17/34   (2006.01)

(52) U.S. Cl.
CPC ...... A61B 17/3423 (2013.01); A61B 17/3439 (2013.01); A61B 2017/3488 (2013.01); A61B 2560/04 (2013.01)

(58) Field of Classification Search
None
See application file for complete search history.

(56) References Cited

U.S. PATENT DOCUMENTS 397,060 A   1/1889   Knapp
512,456 A   1/1894   Sadikova
(Continued)

FOREIGN PATENT DOCUMENTS

EP   0480653 A1   4/1992
EP   0610099 A2   8/1994
(Continued)

Primary Examiner — Jan Christopher L Merene
(74) Attorney, Agent, or Firm — Draft Masters IP, LLC

(57) ABSTRACT

A surgical access device includes a cannula body and a fixation mechanism. The cannula body includes a housing, and an elongated portion extending distally from the housing and defining a longitudinal axis. The fixation mechanism includes a flange, a fixation sleeve, and a proximal sleeve. The flange is rotatable about the longitudinal axis. The fixation sleeve extends distally from the flange and radially surrounds a portion of the elongated portion of the cannula body. The proximal sleeve extends distally from the flange and radially surrounds a proximal portion of the fixation sleeve. Rotation of the flange causes a radially-expandable portion of the fixation sleeve to move between a first position defining a first gap between the radially-expandable portion and the elongated portion, and a second position defining a second, greater, gap between the radially-expandable portion and the elongated portion.

19 Claims, 7 Drawing Sheets

(56) References Cited

U.S. PATENT DOCUMENTS

| | | | |
|---|---|---|---|
| 1,213,005 A | 1/1917 | Pillsbury |
| 2,912,981 A | 11/1959 | Keough |
| 2,936,760 A | 5/1960 | Gains |
| 3,039,468 A | 6/1962 | Price |
| 3,050,066 A | 8/1962 | Koehn |
| 3,253,594 A | 5/1966 | Matthews et al. |
| 3,397,699 A | 8/1968 | Kohl |
| 3,545,443 A | 12/1970 | Ansari et al. |
| 3,713,447 A | 1/1973 | Adair |
| 3,774,596 A | 11/1973 | Cook |
| 3,800,788 A | 4/1974 | White |
| 3,882,852 A | 5/1975 | Sinnreich |
| 3,896,816 A | 7/1975 | Mattler |
| 3,961,632 A | 6/1976 | Moossun |
| RE29,207 E | 5/1977 | Bolduc et al. |
| 4,083,369 A | 4/1978 | Sinnreich |
| 4,217,889 A | 8/1980 | Radovan et al. |
| 4,243,050 A | 1/1981 | Littleford |
| 4,276,874 A | 7/1981 | Wolvek et al. |
| 4,312,353 A | 1/1982 | Shahbabian |
| 4,327,709 A | 5/1982 | Hanson et al. |
| 4,345,606 A | 8/1982 | Littleford |
| 4,411,654 A | 10/1983 | Boarini et al. |
| 4,416,267 A | 11/1983 | Garren et al. |
| 4,490,137 A | 12/1984 | Moukheibir |
| 4,496,345 A | 1/1985 | Hasson |
| 4,574,806 A | 3/1986 | McCarthy |
| 4,581,025 A | 4/1986 | Timmermans |
| 4,596,554 A | 6/1986 | Dastgeer |
| 4,596,559 A | 6/1986 | Fleischhacker |
| 4,608,965 A | 9/1986 | Anspach, Jr. et al. |
| 4,644,936 A | 2/1987 | Schiff |
| 4,654,030 A | 3/1987 | Moll et al. |
| 4,685,447 A | 8/1987 | Iversen et al. |
| 4,701,163 A | 10/1987 | Parks |
| 4,738,666 A | 4/1988 | Fuqua |
| 4,769,038 A | 9/1988 | Bendavid et al. |
| 4,772,266 A | 9/1988 | Groshong |
| 4,779,611 A | 10/1988 | Grooters et al. |
| 4,784,133 A | 11/1988 | Mackin |
| 4,793,348 A | 12/1988 | Palmaz |
| 4,798,205 A | 1/1989 | Bonomo et al. |
| 4,800,901 A | 1/1989 | Rosenberg |
| 4,802,479 A | 2/1989 | Haber et al. |
| 4,813,429 A | 3/1989 | Eshel et al. |
| 4,840,613 A | 6/1989 | Balbierz |
| 4,854,316 A | 8/1989 | Davis |
| 4,861,334 A | 8/1989 | Nawaz |
| 4,865,593 A | 9/1989 | Ogawa et al. |
| 4,869,717 A | 9/1989 | Adair |
| 4,888,000 A | 12/1989 | McQuilkin et al. |
| 4,899,747 A | 2/1990 | Garren et al. |
| 4,917,668 A | 4/1990 | Haindl |
| 4,931,042 A | 6/1990 | Holmes et al. |
| 4,955,895 A | 9/1990 | Sugiyama et al. |
| 5,002,557 A | 3/1991 | Hasson |
| 5,009,643 A | 4/1991 | Reich et al. |
| 5,030,206 A | 7/1991 | Lander |
| 5,030,227 A | 7/1991 | Rosenbluth et al. |
| 5,074,871 A | 12/1991 | Groshong |
| 5,098,392 A | 3/1992 | Fleischhacker et al. |
| 5,104,383 A | 4/1992 | Shichman |
| 5,116,318 A | 5/1992 | Hillstead |
| 5,116,357 A | 5/1992 | Eberbach |
| 5,122,122 A | 6/1992 | Allgood |
| 5,122,155 A | 6/1992 | Eberbach |
| 5,137,512 A | 8/1992 | Burns et al. |
| 5,141,494 A | 8/1992 | Danforth et al. |
| 5,141,515 A | 8/1992 | Eberbach |
| 5,147,302 A | 9/1992 | Euteneuer et al. |
| 5,147,316 A | 9/1992 | Castillenti |
| 5,147,374 A | 9/1992 | Fernandez |
| 5,158,545 A | 10/1992 | Trudell et al. |
| 5,159,925 A | 11/1992 | Neuwirth et al. |
| 5,163,949 A | 11/1992 | Bonutti |
| 5,176,692 A | 1/1993 | Wilk et al. |
| 5,176,697 A | 1/1993 | Hasson |
| 5,183,463 A | 2/1993 | Debbas |
| 5,188,596 A | 2/1993 | Condon et al. |
| 5,188,630 A | 2/1993 | Christoudias |
| 5,195,507 A | 3/1993 | Bilweis |
| 5,201,742 A | 4/1993 | Hasson |
| 5,201,754 A | 4/1993 | Crittenden et al. |
| 5,209,725 A | 5/1993 | Roth |
| 5,215,526 A | 6/1993 | Deniega et al. |
| 5,222,970 A | 6/1993 | Reeves |
| 5,226,890 A | 7/1993 | Ianniruberto et al. |
| 5,232,446 A | 8/1993 | Arney |
| 5,232,451 A | 8/1993 | Freitas et al. |
| 5,234,454 A | 8/1993 | Bangs |
| 5,250,025 A | 10/1993 | Sosnowski et al. |
| 5,258,026 A | 11/1993 | Johnson et al. |
| 5,269,753 A | 12/1993 | Wilk |
| 5,290,249 A | 3/1994 | Foster et al. |
| 5,308,327 A | 5/1994 | Heaven et al. |
| 5,309,896 A | 5/1994 | Moll et al. |
| 5,312,417 A * | 5/1994 | Wilk .................. A61B 17/3439 606/1 |
| 5,314,443 A | 5/1994 | Rudnick |
| 5,318,012 A | 6/1994 | Wilk |
| 5,330,497 A | 7/1994 | Freitas et al. |
| 5,342,307 A | 8/1994 | Euteneuer et al. |
| 5,346,504 A | 9/1994 | Ortiz et al. |
| 5,359,995 A | 11/1994 | Sewell, Jr. |
| 5,361,752 A | 11/1994 | Moll et al. |
| 5,370,134 A | 12/1994 | Chin et al. |
| 5,383,889 A | 1/1995 | Warner et al. |
| 5,397,311 A | 3/1995 | Walker et al. |
| 5,402,772 A | 4/1995 | Moll et al. |
| 5,407,433 A | 4/1995 | Loomas |
| 5,431,173 A | 7/1995 | Chin et al. |
| 5,445,615 A | 8/1995 | Yoon |
| 5,468,248 A | 11/1995 | Chin et al. |
| 5,514,091 A | 5/1996 | Yoon |
| 5,514,153 A | 5/1996 | Bonutti |
| 5,540,658 A | 7/1996 | Evans et al. |
| 5,540,711 A | 7/1996 | Kieturakis et al. |
| 5,607,441 A | 3/1997 | Sierocuk et al. |
| 5,607,443 A | 3/1997 | Kieturakis et al. |
| 5,632,761 A | 5/1997 | Smith et al. |
| 5,656,013 A | 8/1997 | Yoon |
| 5,667,479 A | 9/1997 | Kieturakis |
| 5,667,520 A | 9/1997 | Bonutti |
| 5,704,372 A | 1/1998 | Moll et al. |
| 5,707,359 A * | 1/1998 | Bufalini ............. A61B 17/3421 606/198 |
| 5,707,382 A | 1/1998 | Sierocuk et al. |
| 5,713,869 A | 2/1998 | Morejon |
| 5,722,986 A | 3/1998 | Smith et al. |
| 5,728,119 A | 3/1998 | Smith et al. |
| 5,730,748 A | 3/1998 | Fogarty et al. |
| 5,730,756 A | 3/1998 | Kieturakis et al. |
| 5,738,628 A | 4/1998 | Sierocuk et al. |
| 5,755,693 A | 5/1998 | Walker et al. |
| 5,762,604 A | 6/1998 | Kieturakis |
| 5,772,680 A | 6/1998 | Kieturakis et al. |
| 5,779,728 A | 7/1998 | Unsford et al. |
| 5,797,947 A | 8/1998 | Mollenauer |
| 5,803,901 A | 9/1998 | Chin et al. |
| 5,810,867 A | 9/1998 | Zarbatany et al. |
| 5,814,060 A | 9/1998 | Fogarty et al. |
| 5,836,913 A | 11/1998 | Orth et al. |
| 5,836,961 A | 11/1998 | Kieturakis et al. |
| 5,865,802 A | 2/1999 | Yoon et al. |
| 5,882,340 A * | 3/1999 | Yoon .................. A61B 17/3496 604/164.12 |
| 5,893,866 A | 4/1999 | Hermann et al. |
| 5,925,058 A | 7/1999 | Smith et al. |
| 6,361,543 B1 | 3/2002 | Chin et al. |
| 6,368,337 B1 | 4/2002 | Kieturakis et al. |
| 6,375,665 B1 | 4/2002 | Nash et al. |
| 6,379,372 B1 | 4/2002 | Dehdashtian et al. |
| 6,432,121 B1 | 8/2002 | Jervis |
| 6,447,529 B2 | 9/2002 | Fogarty et al. |

(56) References Cited

U.S. PATENT DOCUMENTS

| | | |
|---|---|---|
| 6,468,205 B1 | 10/2002 | Mollenauer et al. |
| 6,506,200 B1 | 1/2003 | Chin |
| 6,514,272 B1 | 2/2003 | Kieturakis et al. |
| 6,517,514 B1 | 2/2003 | Campbell |
| 6,527,787 B1 | 3/2003 | Fogarty et al. |
| 6,540,764 B1 | 4/2003 | Kieturakis et al. |
| 6,796,960 B2 | 9/2004 | Cioanta et al. |
| 8,454,645 B2 | 6/2013 | Criscuolo et al. |
| 10,751,086 B2 | 8/2020 | Shipp et al. |
| 11,672,563 B2 | 6/2023 | Lobo et al. |
| 2005/0159711 A1 | 7/2005 | Kathrani et al. |
| 2008/0306442 A1 | 12/2008 | Bardsley et al. |
| 2011/0144440 A1 | 6/2011 | Cropper et al. |
| 2016/0278758 A1 | 9/2016 | Osman |
| 2019/0307486 A1 | 10/2019 | Buyda et al. |

FOREIGN PATENT DOCUMENTS

| | | |
|---|---|---|
| EP | 0880939 A1 | 12/1998 |
| WO | 9206638 A1 | 4/1992 |
| WO | 9218056 A1 | 10/1992 |
| WO | 9221293 A1 | 12/1992 |
| WO | 9221295 A1 | 12/1992 |
| WO | 9309722 A1 | 5/1993 |
| WO | 9721461 A1 | 6/1997 |
| WO | 9912602 A1 | 3/1999 |
| WO | 0126724 A2 | 4/2001 |
| WO | 02096307 A2 | 12/2002 |
| WO | 2004032756 A2 | 4/2004 |

\* cited by examiner

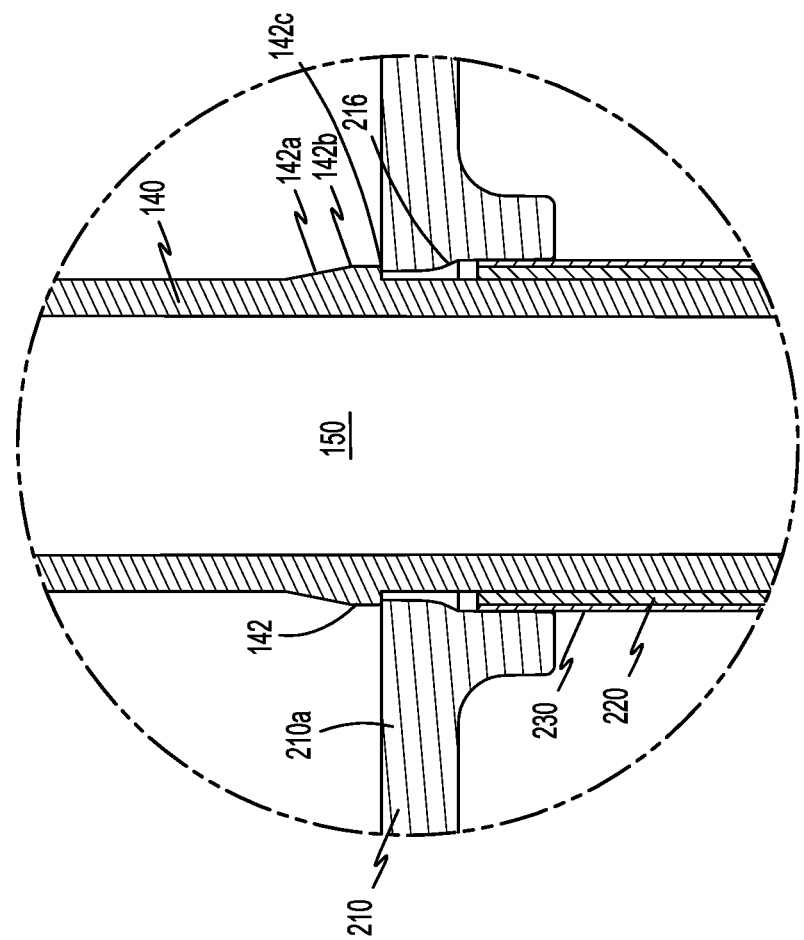
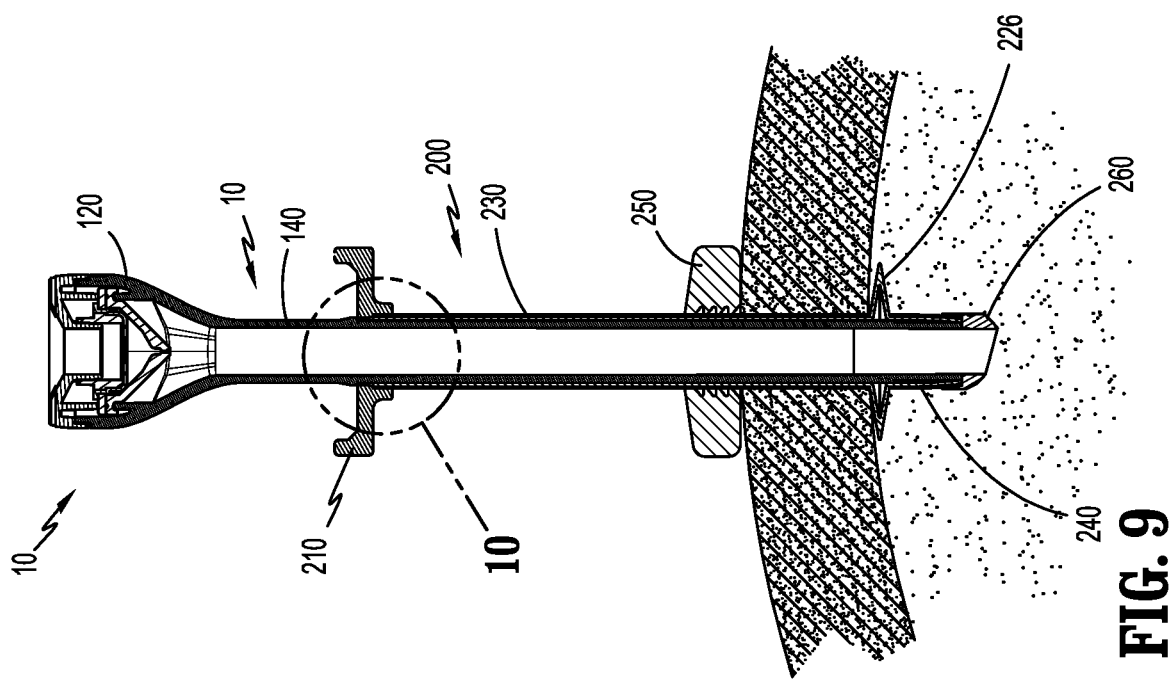

SURGICAL ACCESS DEVICE WITH ROTATABLY ACTUATED FIXATION MECHANISM

CROSS-REFERENCE TO RELATED APPLICATION

The present application is a continuation of U.S. patent application Ser. No. 16/784,662, filed on Feb. 7, 2020, the entire contents of which are incorporated herein by reference.

BACKGROUND

Technical Field

The present disclosure relates to a surgical access device. More particularly, the present disclosure relates to a surgical access device having a rotatably actuated fixation mechanism to help maintain its position relative to a patient during a surgical procedure.

Background of Related Art

In minimally invasive surgical procedures, including endoscopic and laparoscopic surgeries, a surgical access device permits the introduction of a variety of surgical instruments into a body cavity or opening. A surgical access device (e.g., a cannula) is introduced through an opening in tissue (i.e. a naturally occurring orifice or an incision) to provide access to an underlying surgical site in the body. The incision is typically made using an obturator having a blunt or sharp tip that has been inserted within the passageway of the surgical access device. For example, a cannula has a tube of rigid material with a thin wall construction, through which an obturator may be passed. The obturator is utilized to penetrate a body wall, such as an abdominal wall, or to introduce the surgical access device through the body wall, and is then removed to permit introduction of surgical instrumentation through the surgical access device to perform the surgical procedure.

During these procedures, it may be challenging to maintain the position of the surgical access device with respect to the body wall, particularly when exposed to a pressurized environment. To help maintain the position of the surgical access device with respect to the body wall, an expandable anchor or fixation mechanism disposed near a distal end of the surgical access device is occasionally used. Expanding such an anchor while the surgical access device is within the body helps prevent the surgical access device from undesired movement with respect to the body.

Accordingly, it may be helpful to provide a fixation mechanism that is deployed via rotation of a flange, as opposed to longitudinal movement of a flange, for instance, to help maintain the longitudinal position of the surgical access device with respect to the patient.

SUMMARY

The present disclosure relates to a surgical access device including a cannula body and a fixation mechanism. The cannula body includes a housing and an elongated portion extending distally from the housing. The elongated portion defines a longitudinal axis and defines a channel extending therethrough. The fixation mechanism is disposed in mechanical cooperation with the elongated portion of the cannula body, and includes a flange, a fixation sleeve, and a proximal sleeve. The flange is rotatable about the longitudinal axis relative to the elongated portion of the cannula body. The fixation sleeve extends distally from the flange and radially surrounds a portion of the elongated portion of the cannula body. The fixation sleeve includes a proximal portion, a distal portion, and a radially-expandable portion. The proximal sleeve extends distally from the flange and radially surrounds the proximal portion of the fixation sleeve. Rotation of the flange about the longitudinal axis relative to the elongated portion of the cannula body causes the radially-expandable portion of the fixation sleeve to move between a first position defining a first gap between the radially-expandable portion of the fixation sleeve and the elongated portion of the cannula body, and a second position defining a second gap between the radially-expandable portion of the fixation sleeve and the elongated portion of the cannula body. The second gap is greater than the first gap.

In aspects, the fixation mechanism may include a distal sleeve radially surrounding the distal portion of the fixation sleeve.

The radially-expandable portion of the fixation sleeve may be disposed between the proximal portion of the fixation sleeve and the distal portion of the fixation sleeve.

In aspects, the radially-expandable portion of the fixation sleeve may be disposed distally of the proximal sleeve.

Additionally, the fixation mechanism may include a distal sleeve radially surrounding the distal portion of the fixation sleeve. The radially-expandable portion of the fixation sleeve may be disposed distally of the proximal sleeve and proximally of the distal sleeve.

In aspects, the fixation sleeve may be made from at least one of mesh or a shape-memory material.

In additional aspects, the proximal sleeve may be made from at least one of a transparent material or a translucent material. Additionally, the fixation mechanism may include a distal sleeve radially surrounding the distal portion of the fixation sleeve. The distal sleeve may be made from at least one of a transparent material or a translucent material.

In aspects, the surgical access device may include an anchor engaged with the elongated portion of the cannula body. The anchor may be disposed proximally of the radially-expandable portion of the fixation sleeve. The anchor may be longitudinally translatable relative to the elongated portion of the cannula body. The anchor may be longitudinally translatable relative to the fixation sleeve of the fixation mechanism.

In aspects, the surgical access device may include a distal tip engaged with a distal end of the fixation sleeve.

In aspects, the elongated portion of the cannula body may include a raised stop configured to engage the flange of the fixation mechanism. The raised stop may define an annular shelf. In aspects, the flange may be movable between a first position where a proximal wall of the flange is disposed proximally of the annular shelf of the raised stop, and a second position where the proximal wall of the flange is disposed distally of the annular shelf of the raised stop. Additionally, rotation of the flange about the longitudinal axis relative to the elongated portion of the cannula body may cause the flange to move between its first position and its second position.

The present disclosure also relates to a fixation mechanism for use with a surgical access device. The fixation mechanism includes a flange, a fixation sleeve, a proximal sleeve, and a distal sleeve. The flange defines a passageway therethrough, and defines a longitudinal axis. The fixation sleeve extends distally from the flange and includes a proximal portion, a radially-expandable portion, and a distal portion. The proximal sleeve extends distally from the flange and radially surrounds the proximal portion of the fixation sleeve. The distal sleeve radially surrounds the distal portion of the fixation sleeve. Rotation of the flange in a first direction about the longitudinal axis causes the radially-expandable portion of the fixation sleeve to move away from the longitudinal axis.

In aspects, the radially-expandable portion of the fixation sleeve may be disposed distally of the proximal sleeve and proximally of the distal sleeve.

In aspects, the proximal sleeve and the distal sleeve may be made from at least one of a transparent material or a translucent material.

In additional aspects, the fixation sleeve may be made from at least one of mesh or a shape-memory material.

In aspects, the fixation mechanism may include a distal tip secured to a distal end of the fixation sleeve, and secured to the distal sleeve.

DESCRIPTION OF THE DRAWINGS

Various embodiments of the present disclosure are illustrated herein with reference to the accompanying drawings, wherein:

FIG. 9 is a longitudinal cross-sectional view of the surgical access device taken along section line 9-9 in FIG. 8;

FIG. 10 is an enlarged view of the area of detail indicated in FIG. 9;

DETAILED DESCRIPTION

Figure 1:
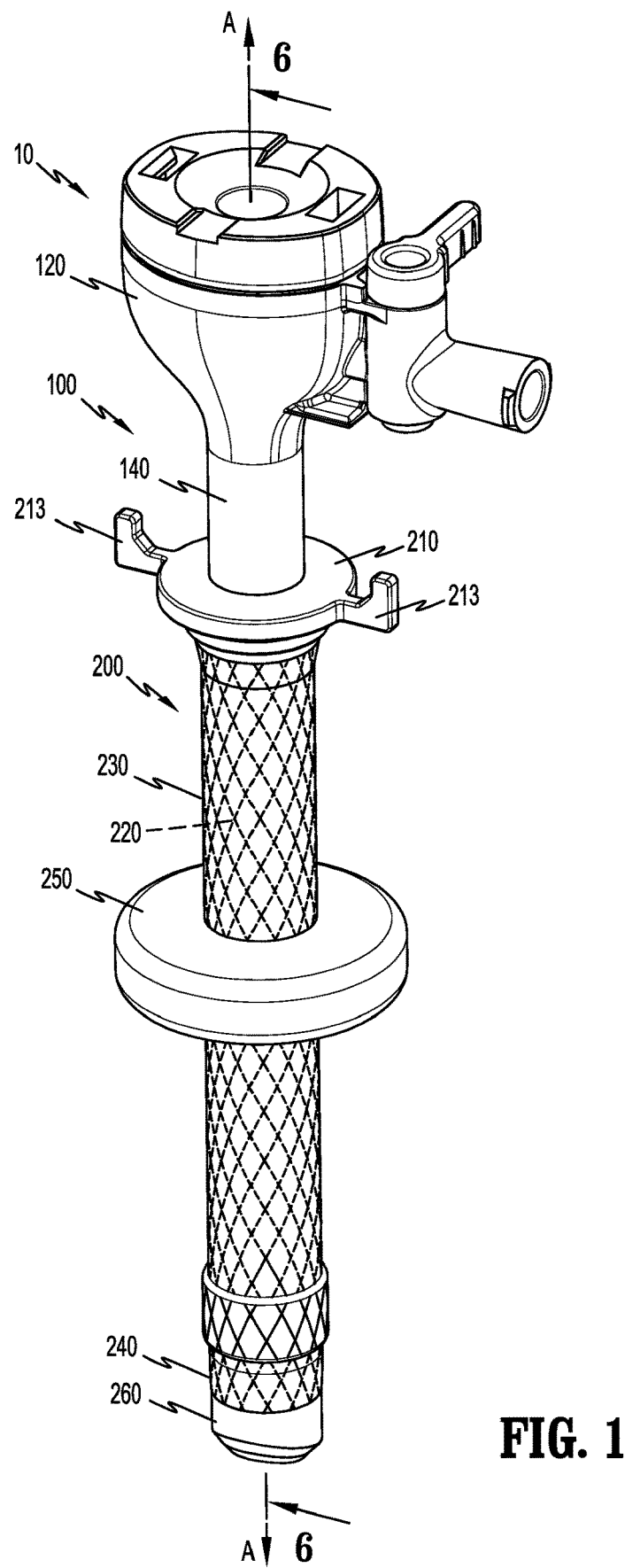
FIG. 1 is a perspective view of a surgical access device illustrating a fixation member in an undeployed configuration.

Aspects of the presently disclosed surgical access device will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component farther away from the user.

Generally, the surgical access device or cannula, often part of a trocar assembly, may be employed during surgery (e.g., laparoscopic surgery) and may, in various aspects, provide for the sealed access of laparoscopic surgical instruments into an insufflated body cavity, such as the abdominal cavity. The cannula is usable with an obturator insertable therethrough. The cannula and obturator are separate components but are capable of being selectively connected together. For example, the obturator may be inserted into and through the cannula until the handle of the obturator engages, e.g., selectively locks into, a proximal housing of the cannula. In this initial position, the trocar assembly is employed to tunnel through an anatomical structure, e.g., the abdominal wall, either by making a new passage through the structure or by passing through an existing opening through the structure. Once the trocar assembly has tunneled through the anatomical structure, the obturator is removed, leaving the cannula in place in the structure, e.g., in the incision created by the trocar assembly. The proximal housing of the cannula may include seals or valves that prevent the escape of insufflation gases from the body cavity, while also allowing surgical instruments to be inserted into the body cavity.

Additionally, the surgical access device of the present disclosure includes a fixation mechanism configured to engage tissue to help maintain the cannula in its position relative to the body during use.

FIGS. 1-10 illustrate an aspect of a surgical access device according to the present disclosure. With initial reference to FIG. 1, the surgical access device 10 includes a cannula body 100 and a fixation mechanism 200. The cannula body 100 includes a proximal housing 120 at its proximal end, and includes an elongated portion 140 extending distally from the proximal housing 120. The elongated portion 140 defines a channel 150 (FIG. 4) extending therethrough, and defines a longitudinal axis "A-A." An obturator (not shown) is insertable through the channel 150 and is engageable with the proximal housing 120, for instance.

Figure 2:
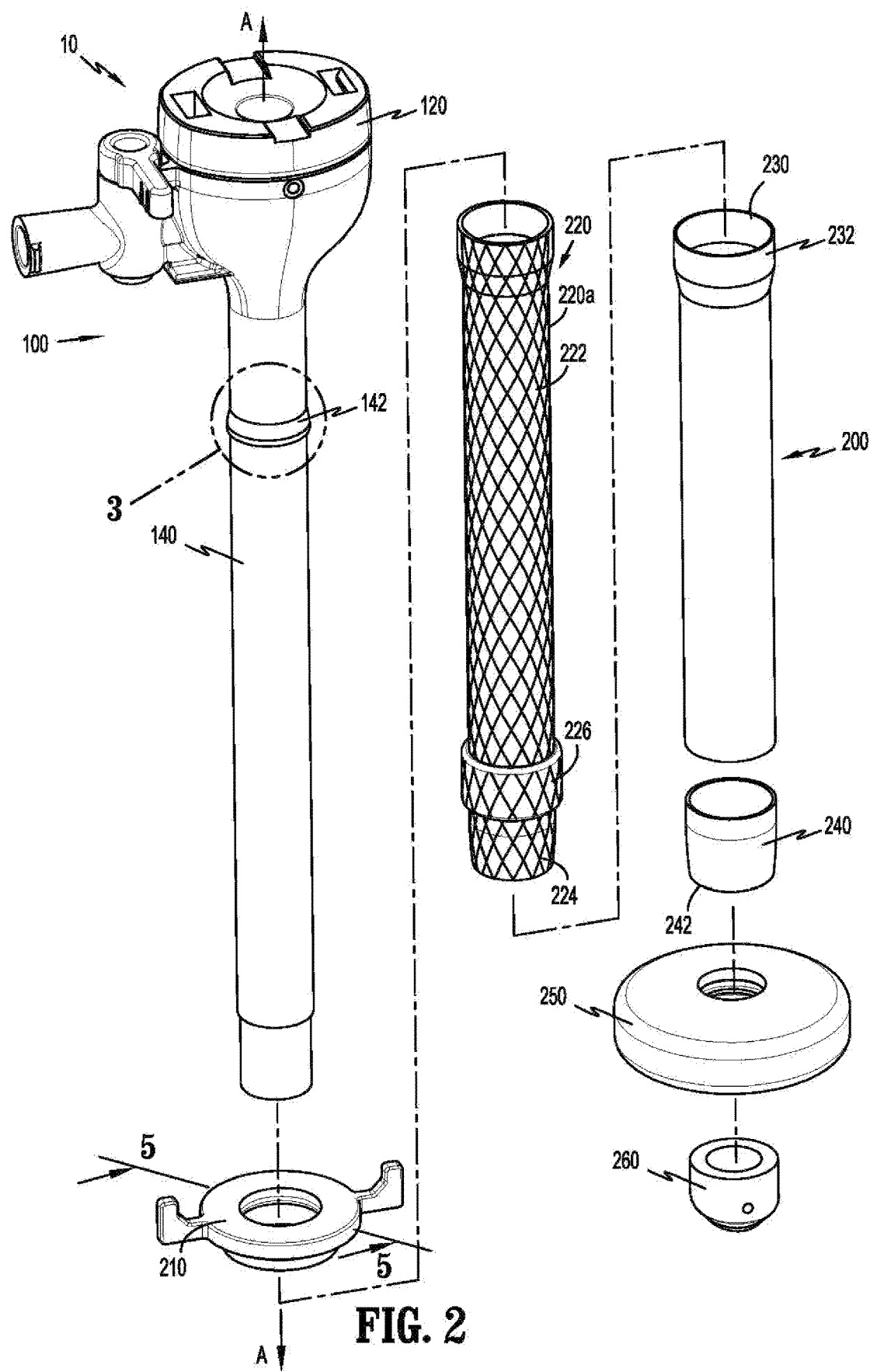
FIG. 2 is an assembly view of the surgical access device of FIG. 1.

With particular reference to FIG. 2, the fixation mechanism 200 is disposed in mechanical cooperation with the elongated portion 140 of the cannula body 100, and includes a flange 210, a fixation sleeve 220, a proximal sleeve 230, a distal sleeve 240, an anchor 250, and a distal tip 260.

Referring to FIGS. 1 and 2, the engagement between the fixation mechanism 200 and the cannula body 100 is shown. The flange 210 is positioned adjacent a raised stop 142 of the elongated portion 140 of the cannula body 100. The fixation sleeve 220 extends distally from the flange 210 and radially surrounds a portion of the elongated portion 140 of the cannula body 100. The proximal sleeve 230 radially surrounds a proximal portion 222 of the fixation sleeve 220. The distal sleeve 240 radially surrounds a distal portion 224 of the fixation sleeve 220. In aspects (such as shown in FIG. 1), at least portions of the proximal sleeve 230 and/or the distal sleeve 240 are made from a transparent or translucent material, such as a plastic film or elastomer, which may facilitate a visual inspection of the fixation sleeve 220, for instance.

As discussed below, the fixation sleeve 220 includes a radially-expandable portion 226 disposed between the proximal portion 222 and the distal portion 224, and which is not radially surrounded by either the proximal sleeve 230 or the distal sleeve 240. The anchor 250 radially surrounds part of the proximal sleeve 230. The distal tip 260 engages a distal end 242 of the distal sleeve 240. Additionally, the flange 210 is secured, e.g., over-molded, to a proximal end 232 of the proximal sleeve 230 and to a proximal end 220a of the fixation sleeve 220, and the distal tip 260 is secured, e.g., over-molded, to a distal end of the distal sleeve 240 and to a distal end of the fixation sleeve 220.

Figure 7:
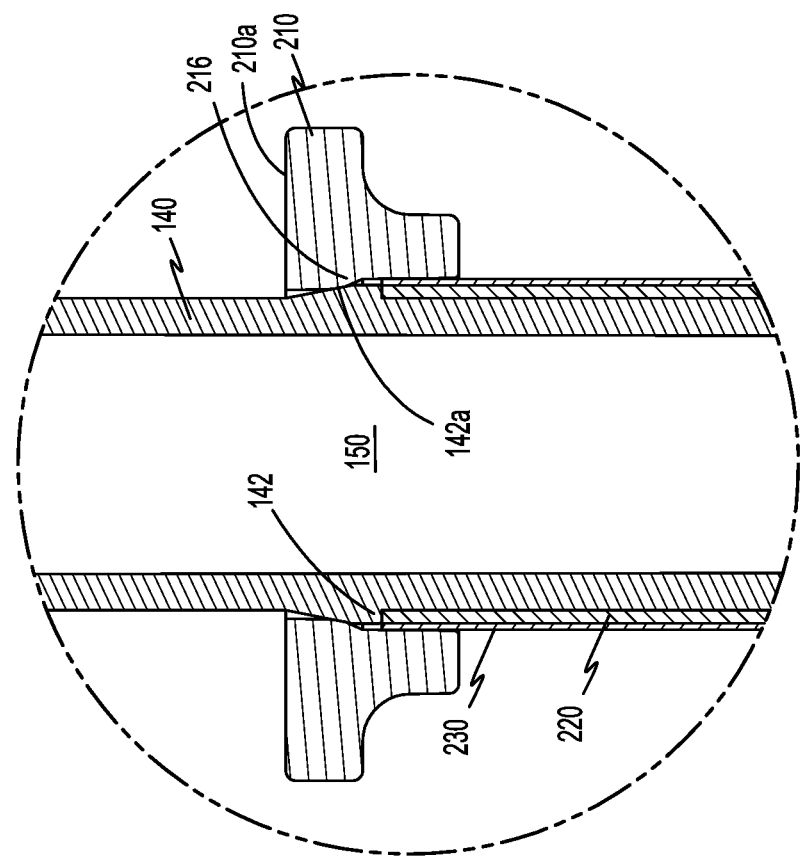
FIG. 7 is an enlarged view of the area of detail indicated in FIG. 6.
Figure 8:
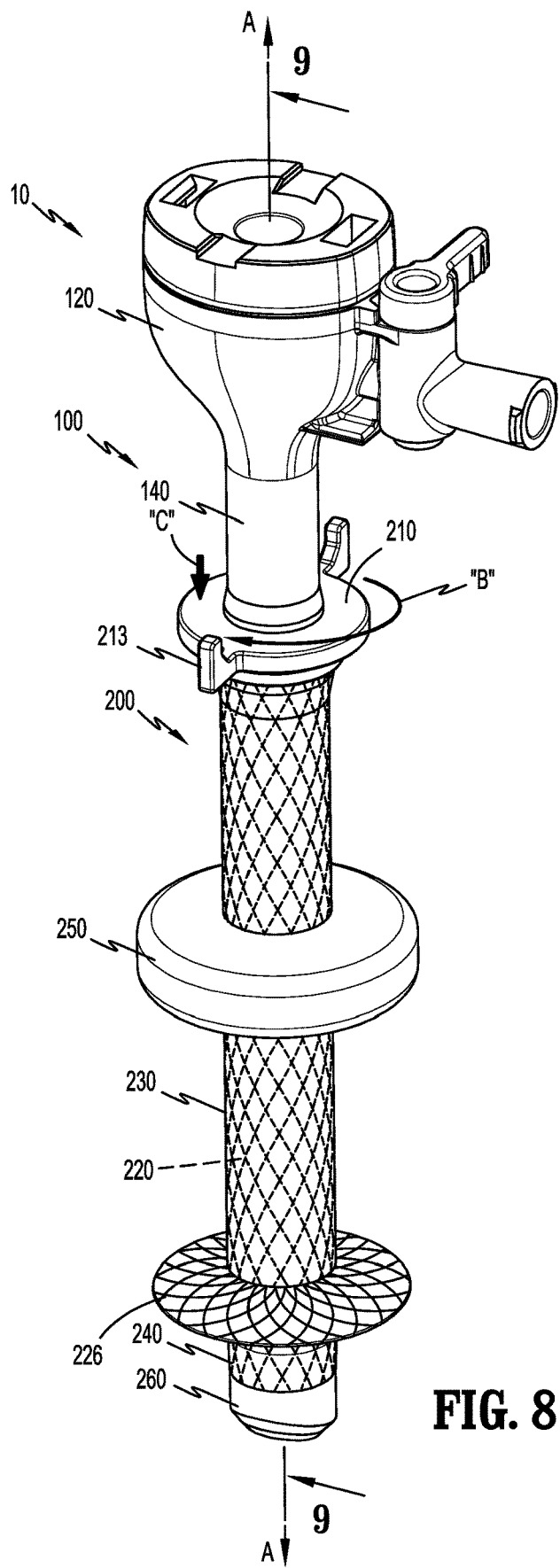
FIG. 8 is a perspective view of the surgical access device of FIG. 1 illustrating the fixation member in a deployed configuration.

The flange 210 is rotatable about the longitudinal axis "A-A" relative to the elongated portion 140 of the cannula body 100, and is longitudinally translatable relative to the elongated portion 140 between a first position where a proximal wall 210a of the flange 210 is disposed proximally of the raised stop 142 (FIGS. 1 and 7), and a second position where the proximal wall 210a of the flange 210 is disposed distally of the raised stop 142 (FIGS. 8 and 10). A predetermined amount of rotation of the flange 210 about the longitudinal axis "A-A" (in the general direction of arrow "B" in FIG. 8) relative to the elongated portion 140 causes the flange 210 to move distally (in the general direction of arrow "C" in FIG. 8) from the first position to the second position. Such movement may be enabled or facilitated by a threaded connection between the flange 210 and the elongated portion 140 of the cannula body 100, and/or by the natural tendencies of the fixation sleeve 220 to contract as it is rotated. In embodiments, the fixation sleeve 220 is made from mesh and/or a shape-memory material.

Figure 6:
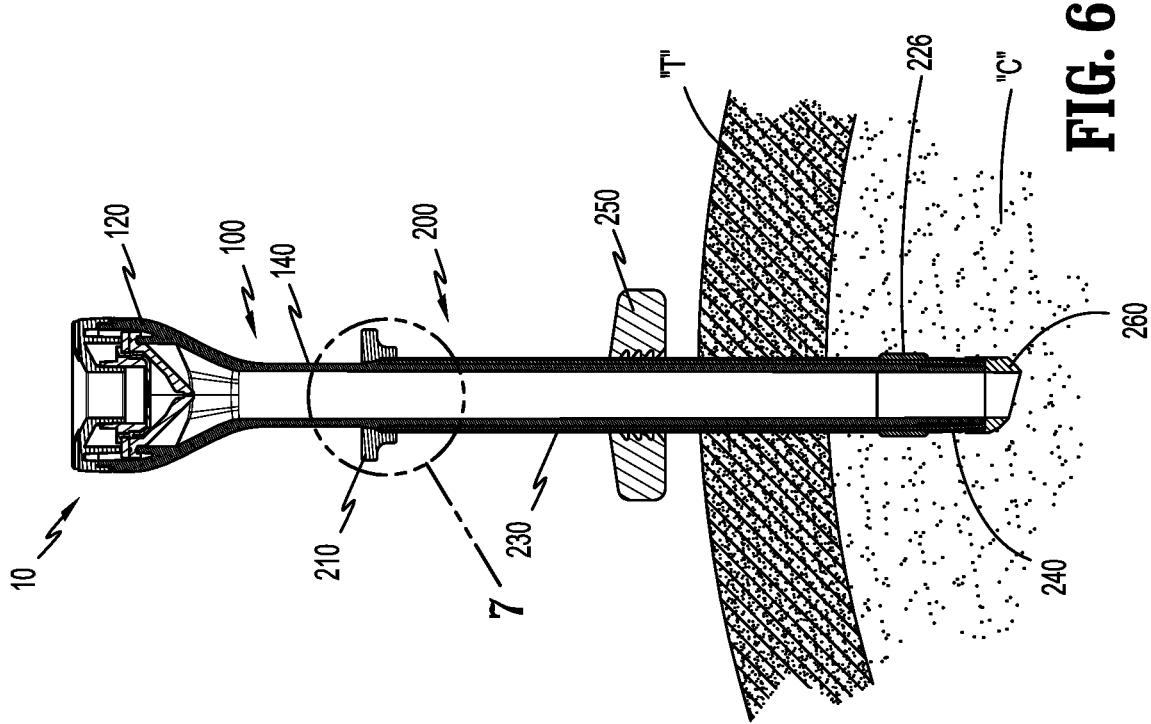
FIG. 6 is a longitudinal cross-sectional view of the surgical access device taken along section line 6-6 in FIG. 1.

The movement of the flange 210 causes the radially-expandable portion 226 of the fixation sleeve 220 to move between a first position (FIGS. 1 and 6) and a second position (FIGS. 8 and 9). In the first position, the radially-expandable portion 226 of the fixation sleeve 220 is non-expanded such that it is adjacent or in contact with the elongated portion 140 of the cannula body 100 (FIGS. 1 and 6) defining a first gap between the radially-expandable portion 226 and the elongated portion 140 of the cannula body 100. With particular reference to FIG. 6, in use, when the radially-expandable portion 226 of the fixation sleeve 220 is in the first position, the distal portion of the elongated portion 140 of the cannula body 100 (i.e., the portion located distally of the anchor 250) is insertable into and removable from a tissue cavity "C."

In the second position, the radially-expandable portion 226 of the fixation sleeve 220 is radially expanded such that it is no longer adjacent or in contact with the elongated portion 140 of the cannula body 100 (FIGS. 8 and 9) defining a second gap between the radially-expandable portion 226 and the elongated portion 140 of the cannula body 100. The second gap is greater than the first gap. In aspects, the radially-expandable portion 226 may be maintained between the first positon and the second position. With particular reference to FIG. 9, in use, when the radially-expandable portion 226 of the fixation sleeve 220 is in the second position, the radially-expandable portion 226 is within the tissue cavity "C" and is adjacent a distal portion of a tissue wall "T," thereby resisting a proximally-directed force acting on the surgical access device 10.

Figure 3:
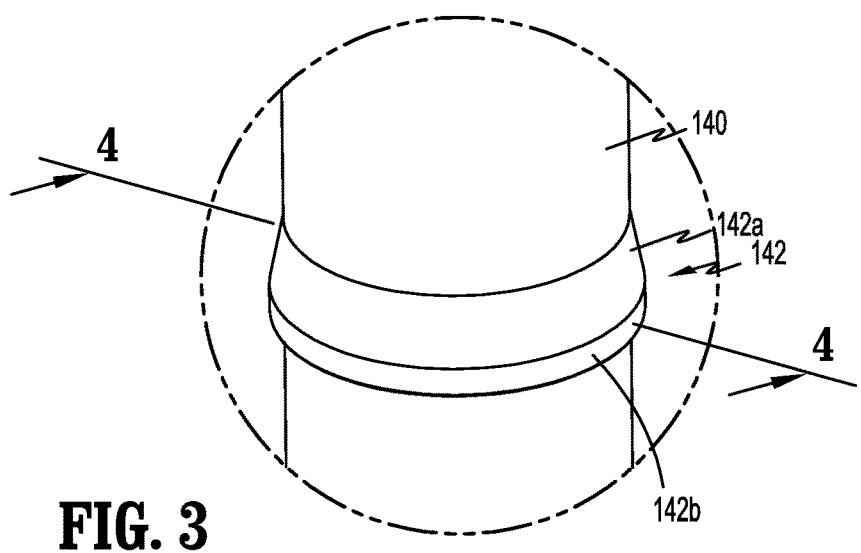
FIG. 3 is an enlarged view of the area of detail indicated in FIG. 2.
Figure 4:
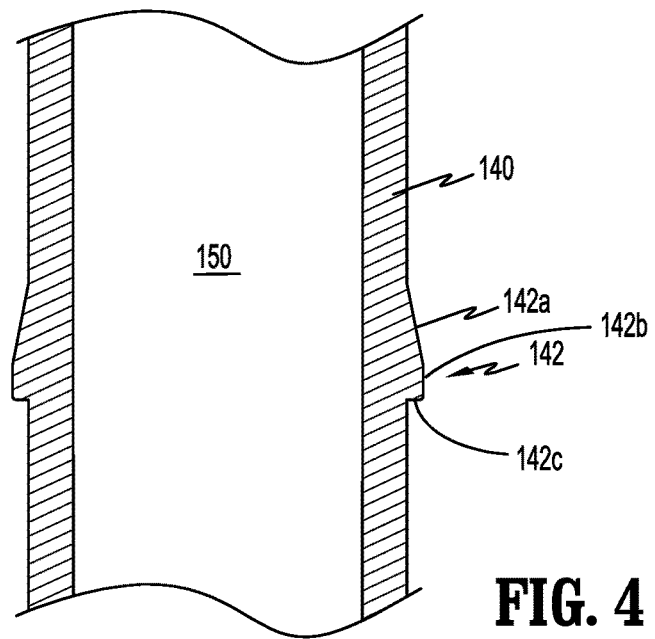
FIG. 4 is a side cross-sectional view of a portion of the surgical access device taken along section line 4-4 in FIG. 3.

With particular reference to FIGS. 3-5, 7 and 10, further details of various features of the fixation mechanism 200 and its engagement with the cannula body 100 are shown. In FIGS. 3 and 4, the raised stop 142 of the elongated portion 140 of the cannula body 100 is shown. The raised stop 142 includes an angled or ramped proximal portion 142a, a linear distal portion 142b, and an annular shelf 142c (FIG. 4) interconnecting the distal portion 142b and the elongated portion 140.

Figure 5:
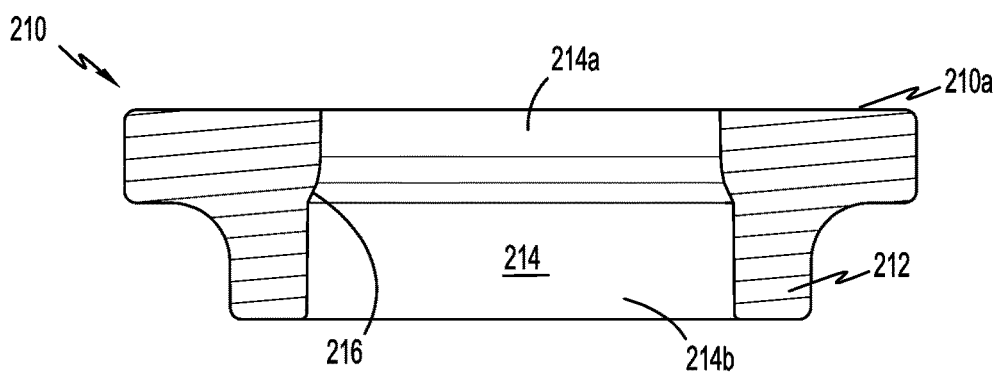
FIG. 5 is a side cross-sectional view of a flange of the surgical access device taken along section line 5-5 in FIG. 2.

FIG. 5 illustrates details of the flange 210. As shown, the flange 210 is ring-like as it includes an annular wall 212 and defines a longitudinal passageway 214 therethrough. As shown in FIG. 1, for example, the annular wall 212 of the flange 210 includes arms 213 to facilitate manipulation of the flange 210 (e.g., rotation thereof) relative to the elongated portion 140 of the cannula body 100. The passageway 214 includes a proximal section 214a and a distal section 214b. The proximal section 214a is narrower than the distal section 214b, and a flange ramp 216 on an inner surface of the annular wall 212 is disposed between the proximal section 214a and the distal section 214b of the passageway.

With particular reference to FIGS. 7 and 10, the engagement between the raised stop 142 of the elongated portion 140 of the cannula body 100 and the flange 210 is shown. When the flange 210 is in its first position (FIG. 7), the proximal wall 210a of the flange 210 is disposed proximally of the raised stop 142. More particularly, the flange ramp 216 is in contact with the ramped proximal portion 142a of the raised stop 142. To move the flange 210 distally past the raised stop 142 and into its second position (FIG. 10), a user can either push the flange 210 distally relative to the elongated portion 140 (with sufficient force to overcome the frictional engagement between the flange ramp 216 and the ramped proximal portion 142a of the raised stop 142), or, as discussed above, the user can rotate the flange 210 in the first direction (e.g., clockwise) about the longitudinal axis "A-A" relative to the elongated portion 140. Once the flange 210 is in its second position (FIG. 10), the engagement between the proximal wall 210a of the flange 210 and the annular shelf 142c of the raised stop 142 helps maintain the flange 210 in the second position by resisting proximally-directed forces against the fixation sleeve 220, for instance. The flange 210 can be returned to its first position by rotating the flange 210 in a second direction (e.g., counter-clockwise) about the longitudinal axis "A-A" relative to the elongated portion 140.

Figure 12:
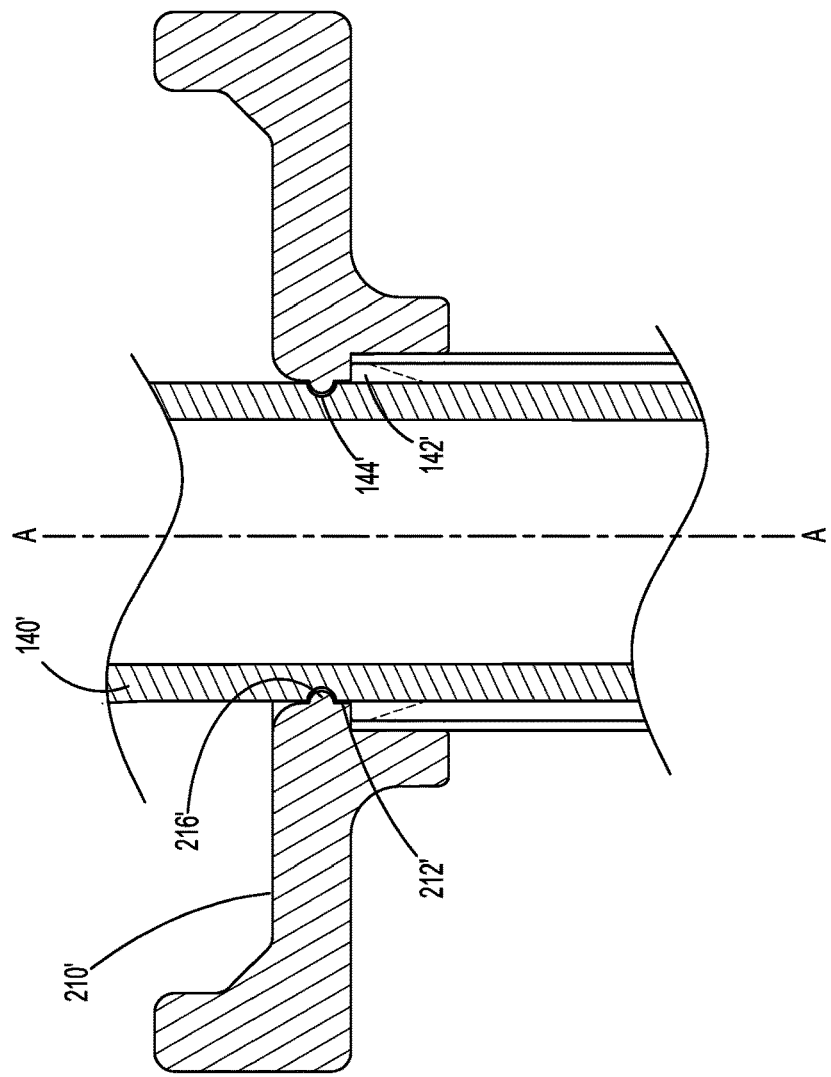
FIG. 12 is a side cross-sectional view of the flange engaged with a portion of the surgical access device of FIG. 11.
Figure 11:
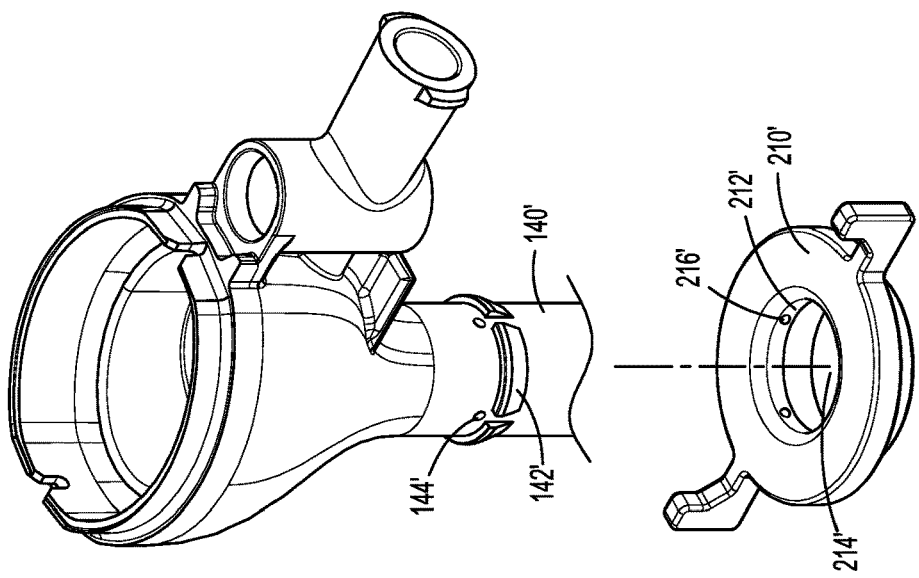
FIG. 11 is an assembly view of a proximal portion of a surgical access device and a flange according to an additional aspect of the present disclosure.

FIGS. 11 and 12 illustrate details of a flange 210' and an elongated portion 140' according to another aspect of the present disclosure. The flange 210' and the elongated portion 140' are configured to work with other elements of the fixation mechanism 200, as discussed above.

The flange 210' is ring-like as it includes an annular wall 212' and defines a longitudinal passageway 214' therethrough. The annular wall 212' of the flange 210' includes a plurality of radially-spaced projections 216' extending radially inward into the longitudinal passageway 214'. The projections 216' are configured to selectively engage corresponding detents 144' disposed on an outer wall of the elongated portion 140'. The detents 144' are positioned proximally of a raised stop 142' of the elongated portion 140'.

In use, when the flange 210' is rotated about the longitudinal axis "A-A" relative to the elongated portion 140', the projections 216' of the flange 210' selectively engage the detents 144' of the elongated portion 140'; more particularly, at least one projection 216'; selectively engages a corresponding detent 144'. The engagement between the projection(s) 216' and the detent(s) 144' helps maintain the rotational position therebetween, which can help maintain the position of the radially-expandable portion 226 of the fixation sleeve 220. Additionally, the raised stop 142' of the elongated portion 140' helps maintain the longitudinal position of the flange 210' with respect to the elongated portion 140'. The radially-expandable portion 226 of the fixation sleeve 220 is either in the first (i.e., non-expanded) position or the second (i.e., expanded) position.

Referring now to FIGS. 1, 2, 6, 8 and 9, further details of the anchor 250 are shown. The anchor 250 is positionable around the cannula body 100 such that the anchor 250 radially surrounds a portion of the proximal sleeve 230. More particularly, the anchor 250 is longitudinally translatable along the proximal sleeve 230 between a first position, where the anchor 250 is farther away from the radially-expandable portion 226 of the fixation sleeve 220 (FIG. 6), and a second position, wherein the anchor 250 is closer to the radially-expandable portion 226 of the fixation sleeve 220 (FIG. 9). The anchor 250 can either have a frictional engagement with the proximal sleeve 230 such that the anchor 250 can be pushed/pulled to move between its first and second positions, or the anchor 250 can be rotationally engaged with the proximal sleeve 230 (e.g., a threaded connection) such that the anchor 250 can be rotated about the longitudinal axis "A-A" relative to the proximal sleeve 230 to move between its first and second positions.

In use, the anchor 250 is initially in the first or proximal position as the distal end of the cannula body 100 is being inserted into and/or positioned within the tissue cavity "C" (FIG. 6). Next, the radially-expandable portion 226 of the fixation sleeve 220 is moved to its second, expanded position, and the cannula body 100 is moved proximally such that the radially-expandable portion 226 of the fixation sleeve 220 contacts the distal portion of the tissue wall "T," for instance. Then, the anchor 250 is moved toward the second or distal position such that the anchor 250 contacts a proximal portion of the tissue wall "T," thereby sandwiching the tissue wall "T" between the anchor 250 and the radially-expandable portion 226 of the fixation sleeve 220 (FIG. 9), and fixing the longitudinal position of the cannula body 100 relative to the tissue wall "T."

The present disclosure also relates to a method of deploying the fixation mechanism 200 of a surgical access device 10. The method includes rotating the flange 210 of the fixation mechanism 200 about the longitudinal axis "A-A" relative to the elongated portion 140 of the cannula body 100 of the surgical access device 10. As discussed above, rotation of the flange 210 causes the radially-expandable portion 226 of the fixation sleeve 220 to move between a first, non-expanded position, and a second, expanded position.

While the above description contains many specifics, these specifics should not be construed as limitations on the scope of the present disclosure, but merely as illustrations of various aspects thereof. Therefore, the above description should not be construed as limiting, but merely as exemplifications of various aspects. Those skilled in the art will envision other modifications within the scope and spirit of the claims appended hereto.

What is claimed is:

1. A fixation mechanism for use with a cannula defining a passageway, the passageway defining a longitudinal axis, the fixation mechanism comprising:
   a flange configured to be arranged around the cannula;
   a fixation sleeve extending distally from the flange, the fixation sleeve defined by an internal surface configured to be arranged adjacent to an external surface of the cannula, the fixation sleeve including a proximal portion, a distal portion, and a radially-expandable portion; and
   a proximal sleeve extending distally from the flange and radially surrounding the proximal portion of the fixation sleeve,
   wherein rotation of the flange about the longitudinal axis causes the radially-expandable portion of the fixation sleeve to move between a first position defining a first gap enclosed between the internal surface of the radially-expandable portion of the fixation sleeve and the external surface of the cannula, and a second position defining a second gap enclosed between the internal surface of the radially-expandable portion of the fixation sleeve and the external surface of the cannula, the second gap being greater than the first gap.

2. The fixation mechanism according to claim 1, further including a distal sleeve radially surrounding the distal portion of the fixation sleeve.

3. The fixation mechanism according to claim 1, wherein the radially-expandable portion of the fixation sleeve is disposed between the proximal portion of the fixation sleeve and the distal portion of the fixation sleeve.

4. The fixation mechanism according to claim 1, wherein the radially-expandable portion of the fixation sleeve is disposed distally of the proximal sleeve.

5. The fixation mechanism according to claim 1, further including a distal sleeve radially surrounding the distal portion of the fixation sleeve, wherein the radially-expandable portion of the fixation sleeve is disposed distally of the proximal sleeve and proximally of the distal sleeve.

6. The fixation mechanism according to claim 1, wherein the fixation sleeve is made from at least one of mesh or a shape-memory material.

7. The fixation mechanism according to claim 1, wherein the proximal sleeve is made from at least one of a transparent material or a translucent material.

8. The fixation mechanism according to claim 7, further including a distal sleeve radially surrounding the distal portion of the fixation sleeve, the distal sleeve being made from at least one of a transparent material or a translucent material.

9. The fixation mechanism according to claim 1, further including an anchor positioned proximally of the radially-expandable portion of the fixation sleeve.

10. The fixation mechanism according to claim 9, wherein the anchor is longitudinally translatable relative to the fixation sleeve.

11. The fixation mechanism according to claim 1, further including a distal tip engaged with a distal end of the fixation sleeve.

12. A fixation mechanism for use with a cannula defining a passageway, the passageway defining a longitudinal axis, the fixation mechanism comprising:
   a flange configured to be arranged around the cannula;
   a fixation sleeve extending distally from the flange, the fixation sleeve defined by an internal surface configured to be arranged adjacent to the external surface of the cannula, and the fixation sleeve including a proximal portion, a radially-expandable portion, and a distal portion; and
   a proximal sleeve extending distally from the flange, radially surrounding the proximal portion of the fixation sleeve, and disposed proximally of the radially-expandable portion of the fixation sleeve,
   wherein rotation of the flange in a first direction about the longitudinal axis causes the radially-expandable portion of the fixation sleeve to move away from the longitudinal axis, forming a gap enclosed between the external surface of the cannula and the internal surface of the radially expandable portion of the fixation sleeve.

13. The fixation mechanism according to claim 12, wherein the proximal sleeve is made from at least one of a transparent material or a translucent material.

14. The fixation mechanism according to claim 12, wherein the fixation sleeve is made from at least one of mesh or a shape-memory material.

15. The fixation mechanism according to claim 12, further including a distal tip secured to a distal end of the fixation sleeve.

16. A surgical access device, comprising:
   a cannula defining a passageway, the passageway defining a longitudinal axis; and
   a fixation mechanism comprising:

a flange defined by a proximal end and a distal end, the flange configured for receiving the cannula;

a fixation sleeve extending distally from the flange and including a proximal portion, a radially-expandable portion, and a distal portion, the fixation sleeve being arranged around the external surface of the cannula; and a proximal sleeve extending distally from the flange and radially surrounding the proximal portion of the fixation sleeve, a proximal portion of the proximal sleeve being fixed from longitudinal movement relative to the flange, wherein the proximal end of the flange is in direct contact with the external surface of the cannula and the distal end of the flange is fixed to the proximal portion of the fixation sleeve, wherein rotation of the flange in a first direction about the longitudinal axis causes the radially-expandable portion of the fixation sleeve to move away from the longitudinal axis.

17. The surgical access device according to claim 16, wherein the radially-expandable portion of the fixation sleeve is disposed between the proximal portion of the fixation sleeve and the distal portion of the fixation sleeve.

18. The surgical access device according to claim 16, wherein the radially-expandable portion of the fixation sleeve is disposed distally of the proximal sleeve.

19. The fixation mechanism according to claim 16, further including an anchor positioned proximally of the radially-expandable portion of the fixation sleeve, wherein the anchor is longitudinally translatable relative to the fixation sleeve.

\* \* \* \* \*